United States Patent
Larse (10) Patent No.: US 11,497,182 B2
(45) Date of Patent: *Nov. 15, 2022

(54) METHODS OF MAKING AND USING STRAWBERRY PLANTS RESISTANT TO FUSARIUM OXYSPORUM

(71) Applicant: Sweet Darling Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/143,031

(22) Filed: Jan. 6, 2021

(65) Prior Publication Data

US 2022/0210989 A1    Jul. 7, 2022

(51) Int. Cl.
*A01H 5/08* (2018.01)
*A01H 1/00* (2006.01)
*A01H 1/02* (2006.01)
*A01H 1/04* (2006.01)
*A01H 6/74* (2018.01)

(52) U.S. Cl.
CPC ............ *A01H 1/1255* (2021.01); *A01H 1/021* (2021.01); *A01H 1/045* (2021.01); *A01H 5/08* (2013.01); *A01H 6/7409* (2018.05)

(58) Field of Classification Search
None
See application file for complete search history.

(56) References Cited

U.S. PATENT DOCUMENTS

| | | | |
|---|---|---|---|
| PP25,849 P3 | 9/2015 | Larse | |
| PP27,190 P3 * | 9/2016 | Bagdasarian | A01H 5/08 Plt./209 |
| PP32,800 P3 | 2/2021 | Larse | |
| 2020/0245516 P1 | 7/2020 | Larse | |
| 2021/0051909 A1 | 2/2021 | Larse | |

* cited by examiner

*Primary Examiner* — Phuong T Bui
(74) *Attorney, Agent, or Firm* — Cooley LLP (57) ABSTRACT

The present disclosure provides methods of producing strawberry plants with resistance to *Fusarium* wilt; and, the strawberry plants, and parts thereof, produced using such methods.

11 Claims, 5 Drawing Sheets
(5 of 5 Drawing Sheet(s) Filed in Color)
Specification includes a Sequence Listing.

METHODS OF MAKING AND USING STRAWBERRY PLANTS RESISTANT TO FUSARIUM OXYSPORUM

CROSS-REFERENCE TO RELATED APPLICATION

The present application is related to U.S. patent application Ser. No. 17/092,075, filed on Nov. 6, 2020; U.S. patent application Ser. No. 16/873,069, filed on Jan. 28, 2020 and issued as PP32,800 on Feb. 9, 2021; and U.S. Provisional Patent Application No. 62/797,491, filed on Jan. 28, 2019. Each of these recited patent applications are incorporated by reference herein in its entirety for all purposes.

FIELD

The present disclosure generally relates to the field of agricultural industry, especially production of consumer crops with pathogenic resistance. More particularly, the present disclosure relates to compositions and methods for generating plants that possess traits resistant to fungal pathogens such as the soil-born *Fusarium* fungi and/or that show resistance to diseases caused by said fungal pathogens.

STATEMENT REGARDING SEQUENCE LISTING

The Sequence Listing associated with this application is provided in text format in lieu of a paper copy, and is hereby incorporated by reference into the specification. The name of the text file containing the Sequence Listing is SWEE_029_00US_SeqList_ST25.txt. The text file is 0.5 KB, was created on Jan. 5, 2021, and is being submitted electronically via EFS-Web.

BACKGROUND OF THE DISCLOSURE

Garden strawberry (*Fragaria* x *ananassa*) is a widely grown hybrid species of the genus *Fragaria*. Strawberry fruit is widely appreciated for its characteristic aroma, bright red color, juicy texture and sweetness. It is consumed in large quantities either fresh or in numerous prepared foods, including jams, juices, pies, milkshakes, etc.

Global strawberry production increased by 39.4% between 2008 and 2018. China led worldwide production at 3 million tons in 2018, followed by the United States with 1.3 million tons. Despite having the world's highest average yield/hectare, production in the United States over this time period did not show the sharp increases in production obtained in some other countries, including China. See, e.g., HortDaily, Sep. 23, 2020, Global strawberry production up by almost 40%, online publication.

*Fusarium* wilt, caused by *Fusarium oxysporum* f. sp. *fragariae*, is an important disease of strawberry (*Fragaria* x *ananassa*) that affects production of this crop in many locations throughout the world (Koike and Gordon, 2015, Management of *Fusarium* wilt of strawberry, Crop. Prot. 73:67-72). *Fusarium* wilt is present in all major strawberry production areas in California, and constitutes a significant threat to this $2.6 billion industry, which produces over 80% of the fresh strawberry fruit consumed in the United States. California Department of Food and Agriculture, 2014, California Agricultural Production Statistics, online publication; USDA Economic Research Service, 2015 Yearbook Tables, Fruit and Tree Nut Data, online publication.

There is a continuing need for improved, adapted strawberry germplasm with resistance to *Fusarium* wilt, particularly for large-scale production of strawberry in California. The present disclosure provides improved, adapted, *Fusarium*-resistant germplasm as well as methods of producing and using this germplasm.

The foregoing and other objects and features of the disclosure will become more apparent from the following detailed description, which proceeds with reference to the accompanying figures. Further embodiments, forms, features, aspects, benefits, objects, and advantages of the present application shall become apparent from the detailed description provided herewith. Additional embodiments of the present disclosure will be readily ascertained by one skilled in the art of molecular genetics, plant breeding, plant husbandry, agricultural production, and other plant-related technologies upon reading the present application.

DESCRIPTION OF THE DRAWINGS

The patent or application file contains at least one drawing executed in color. Copies of this patent or patent application publication with color drawing(s) will be provided by the Office upon request and payment of the necessary fee.

The accompanying color photographs depict various characteristics of the cultivar as nearly true as possible to make color reproductions.

SUMMARY OF THE DISCLOSURE

Figure 1:
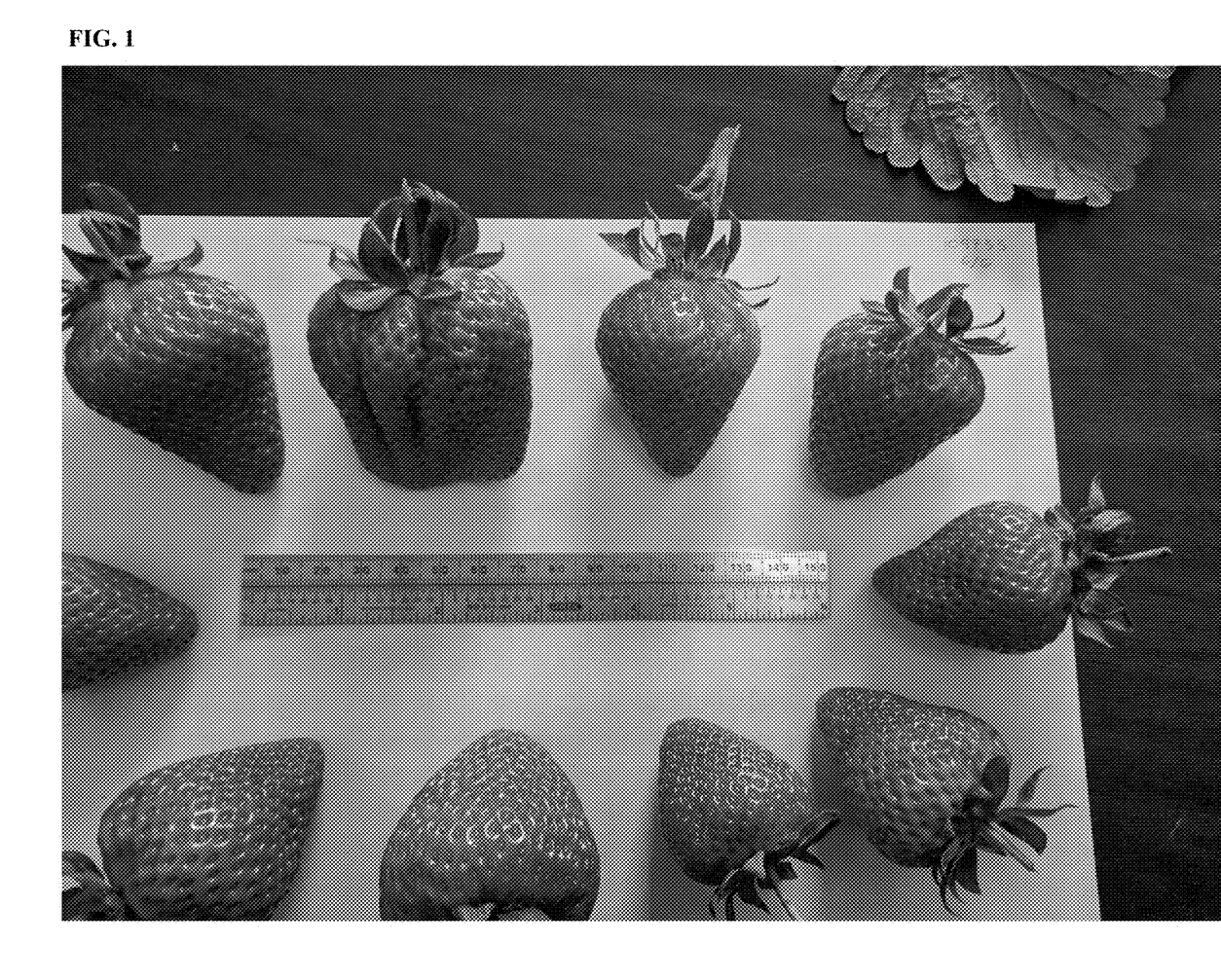
FIG. 1 shows 'Yakima' fruit.
Figure 2:
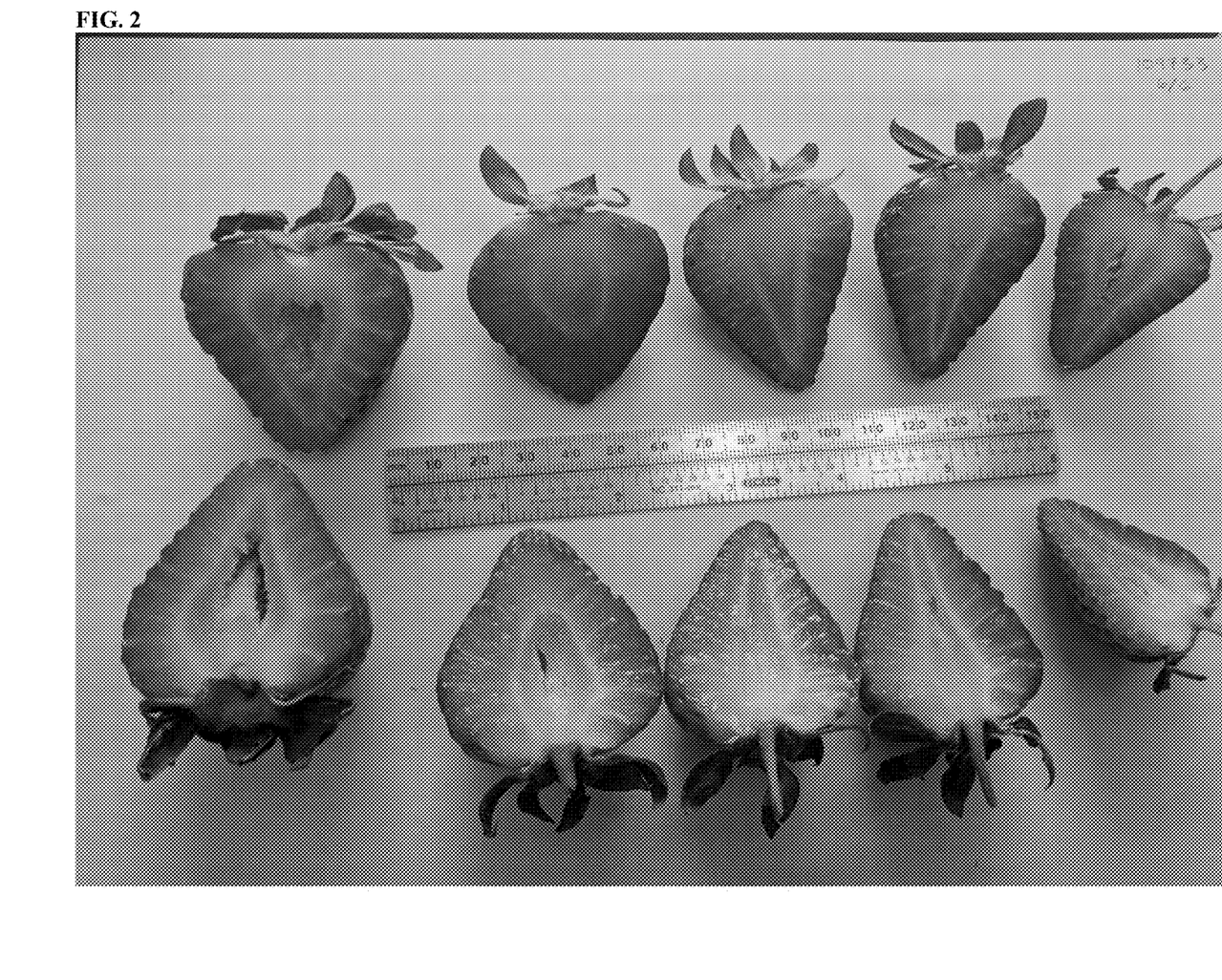
FIG. 2 shows cross section of 'Yakima' fruit.
Figure 3A:
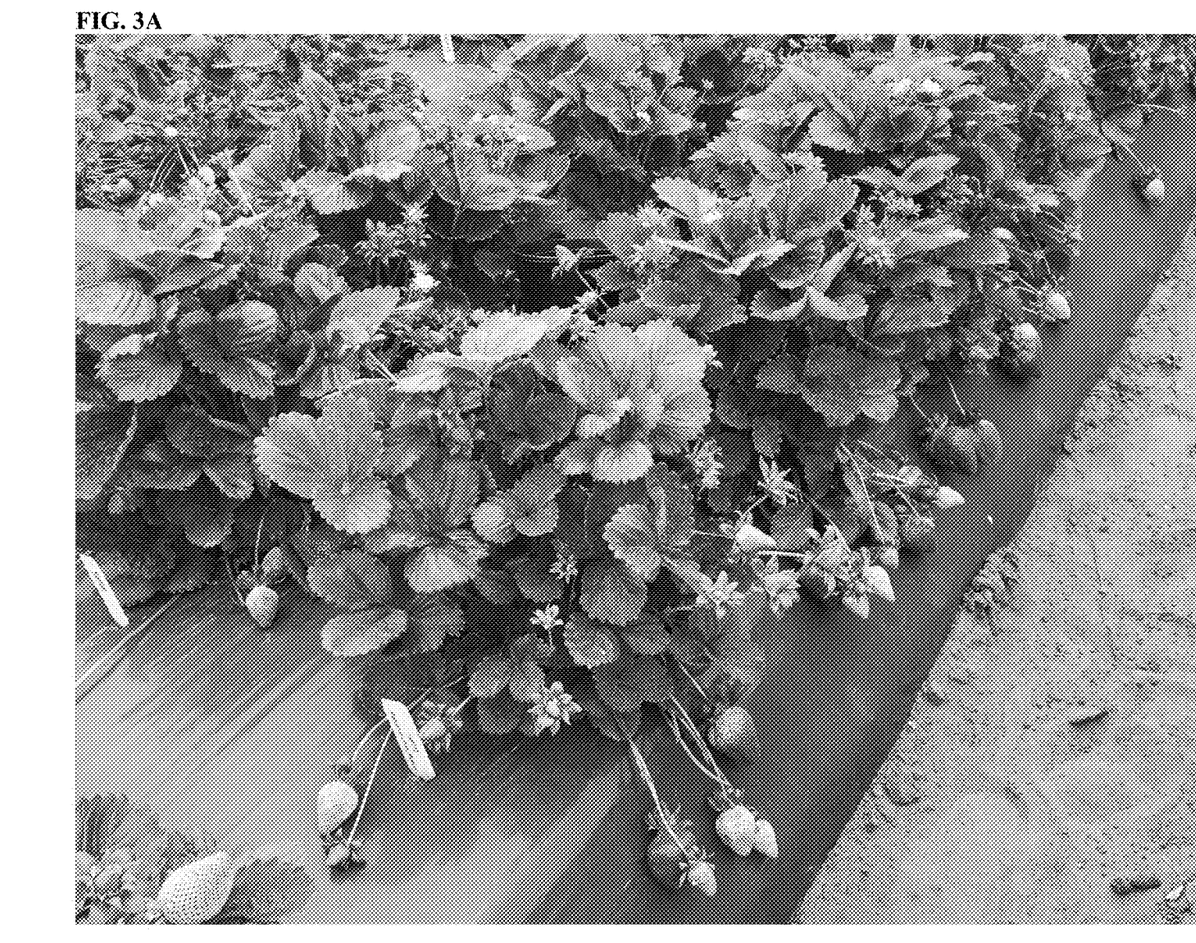
FIG. 3A and FIG. 3B show 'Yakima' strawberry plants with fruit.
Figure 3B:
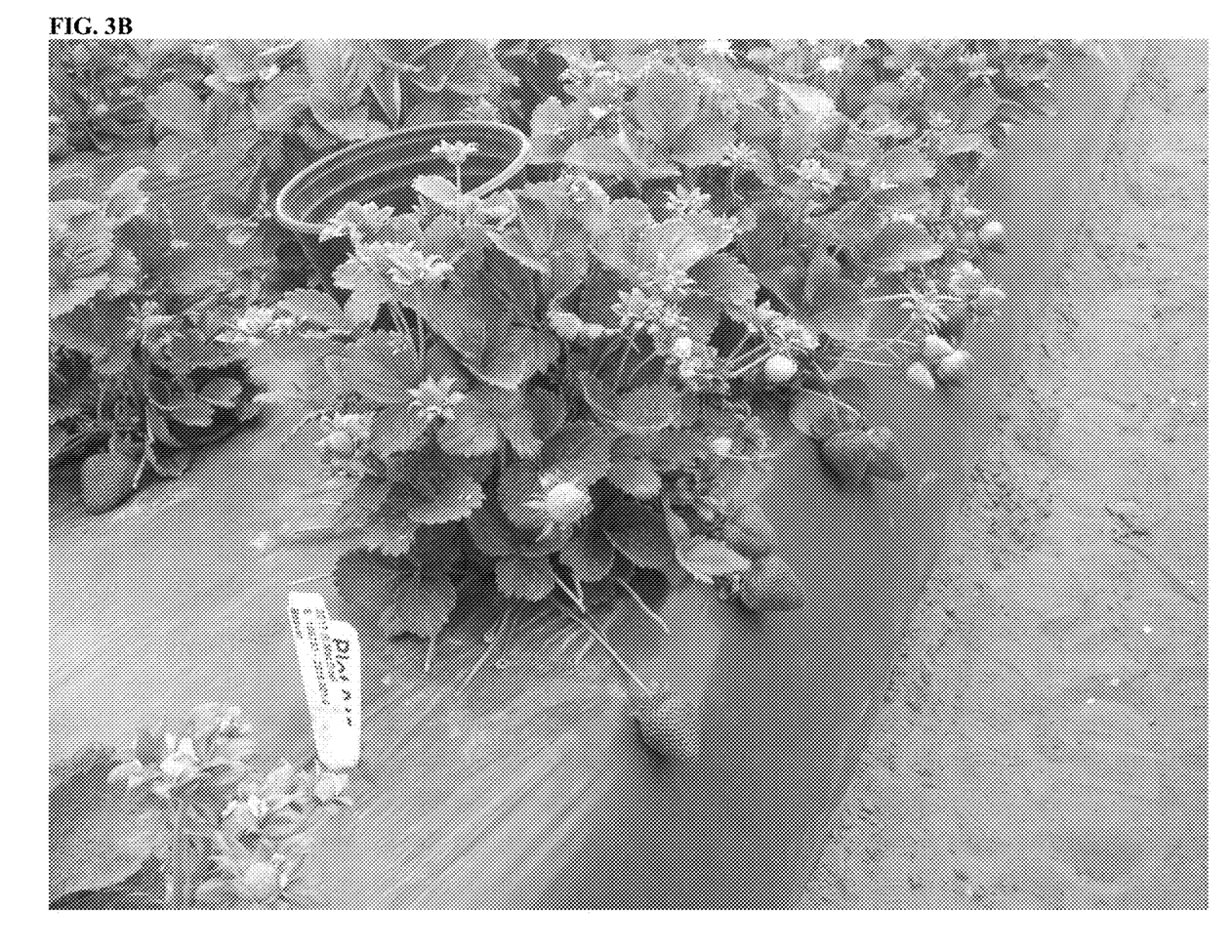
Figure 4:
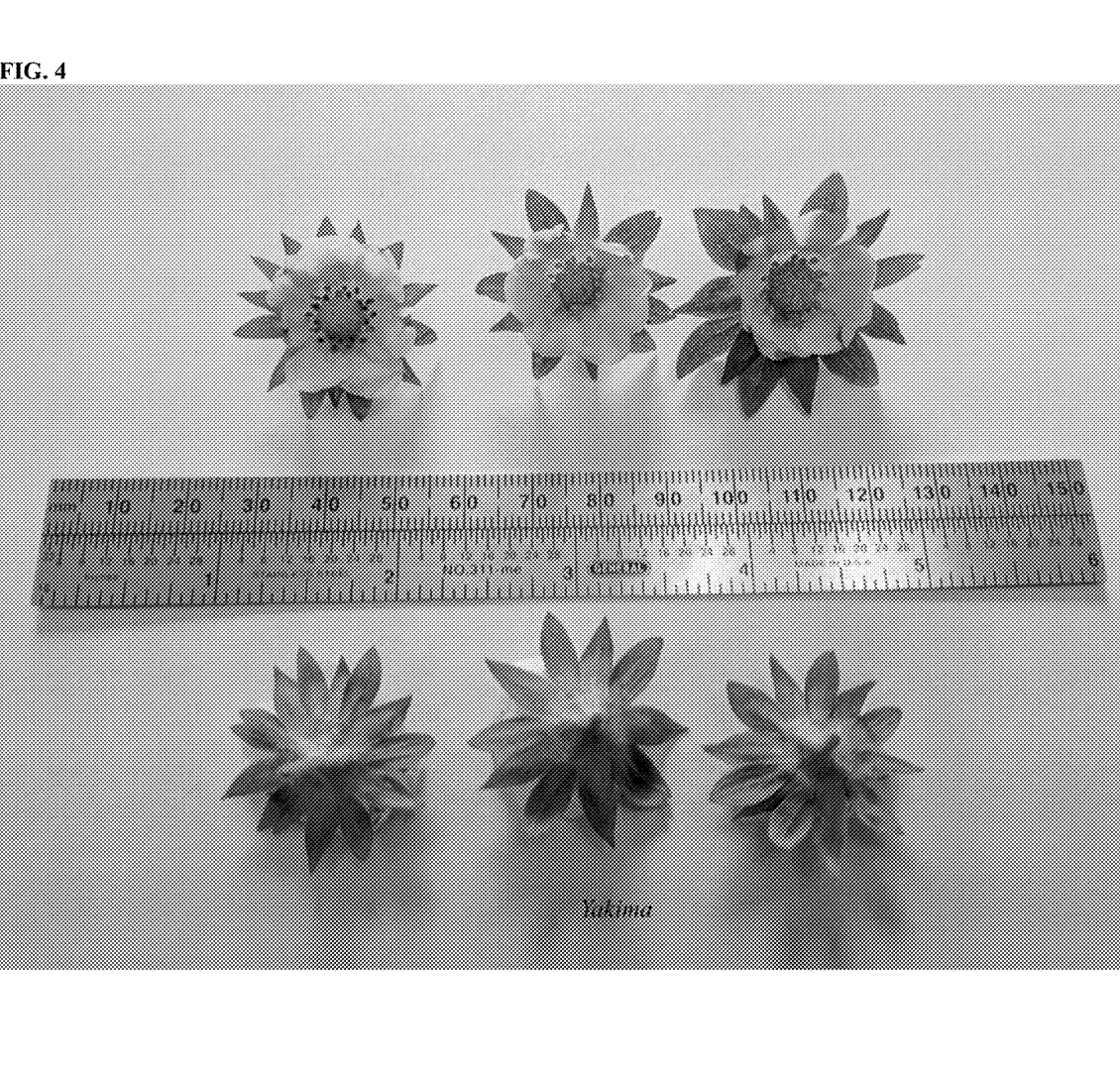
FIG. 4 shows flowers of 'Yakima' strawberry plant variety.

The present disclosure relates to a new and distinct short-day strawberry variety designated as 'Yakima' (a.k.a. '109733') and methods of its use in strawberry production and strawberry breeding.

The present disclosure provides strawberry breeding methods comprising crossing a first strawberry plant with a second strawberry plant to produce progeny plants, growing the progeny plants, and selecting among the progeny plants for progeny plants with resistance to *Fusarium oxysporum*, wherein either the first or second strawberry plant is strawberry cultivar 'Yakima' deposited as NCMA Deposit No. 202107021. In some embodiments of the strawberry breeding methods of the present disclosure, the *Fusarium oxysporum* is *Fusarium oxysporum* f. sp. *fragariae*. In some embodiments of the strawberry breeding methods of the present disclosure, the progeny of the cross that display resistance to *Fusarium oxysporum* f sp. *fragariae* are selected using molecular markers that are designed based on the nucleic acid sequence coding for resistance to *Fusarium oxysporum* f. sp. *fragariae* that is present in the 'Yakima' plant used in the cross. In some embodiments of the strawberry breeding methods of the present disclosure, the progeny plants are selected amongst themselves based on one or more of selection criteria selected from the group consisting of mean fruit height, mean fruit width, mean fruit height to mean fruit width ratio, mean fruit hardness, mean fruit firmness, mean fruit appearance score, mean individual fruit weight in grams per plant, and mean combined fruit weight in grams per plant. In some embodiments of the strawberry breeding methods of the present disclosure, clones are produced of the progeny plants. In further embodiments, the clones are tested for resistance to *Fusarium oxysporum*. In some embodiments of the strawberry breeding methods of the present disclosure, the selected progeny plants are crossed with another strawberry plant to produce a strawberry hybrid plant and growing the resultant strawberry hybrid plant. In further embodiments, the progeny of the cross that display resistance to *Fusarium oxysporum* f sp. *fragariae* are selected using molecular markers that are designed based on the nucleic acid sequence coding for resistance to *Fusarium oxysporum* f sp. *fragariae* that is present in the 'Yakima'. In some embodiments of the present disclosure, progeny plants, plant parts or plant cells thereof, are produced.

The present disclosure provides strawberry cultivars having resistance to *Fusarium oxysporum*, wherein the strawberry cultivars genetically trace their resistance to *Fusarium oxysporum* to the strawberry cultivar 'Yakima' deposited as NCMA Deposit No. 202107021. In further embodiments, plant parts of the strawberry cultivars are produced. In some such embodiments, the plant parts are selected from the group of plant parts consisting of stolons, meristems, and fruits.

The present disclosure provides methods for producing hybrid strawberry plants, or parts thereof, comprising crossing two strawberry plants to produce such hybrid strawberry plants and growing the hybrid strawberry plants, wherein at least one of the two strawberry plants is the strawberry cultivar 'Yakima' deposited as NCMA Deposit No. 202107021. In further embodiments, hybrid strawberry plants, plant parts or plant cells thereof, are produced by the methods of the present disclosure. In some embodiments of the present disclosure, the method comprises crossing a plant of the strawberry cultivar 'Yakima' with a different plant of the strawberry cultivar 'Yakima' to produce the hybrid strawberry plants. In further embodiments, hybrid strawberry plants, plant parts or plant cells thereof, are produced by the methods of the present disclosure. In some embodiments of the present disclosure, the methods further comprise selecting among the hybrid strawberry plants for hybrid strawberry plants with resistance to *Fusarium oxysporum*. In some embodiments, the *Fusarium oxysporum* is *Fusarium oxysporum* f sp. *fragariae*. In some embodiments, the hybrid strawberry plants that display resistance to *Fusarium oxysporum* f sp. *fragariae* are selected using molecular markers that are designed based on the nucleic acid sequence coding for resistance to *Fusarium oxysporum* f. sp. *fragariae* that is present in one or both of the 'Yakima' plants used in the cross. In further embodiments, the methods further comprise selecting among the hybrid strawberry plants based on one or more of selection criteria selected from the group consisting of mean fruit height, mean fruit width, mean fruit height to mean fruit width ratio, mean fruit hardness, mean fruit firmness, mean fruit appearance score, mean individual fruit weight in grams per plant, and mean combined fruit weight in grams per plant.

DETAILED DESCRIPTION

I. Definitions

Unless stated otherwise, all technical and scientific terms used herein have the same meaning as commonly understood by those of ordinary skill in the art to which the disclosure belongs. While the following terms are believed to be well understood by one of ordinary skill in the art, the following definitions are set forth to facilitate explanation of the presently disclosed subject matter. Although any methods and materials similar or equivalent to those described herein can be used in the practice or testing of the present disclosure, preferred methods and materials are described. The following terms are defined below. These definitions are for illustrative purposes and are not intended to limit the common meaning in the art of the defined terms.

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used in this specification, the term "and/or" is used in this disclosure to mean either "and" or "or" unless indicated otherwise.

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "traditional plant breeding" refers to the utilization of natural variation found within a plant population as a source for alleles and genetic variants that impart a trait of interest to a given plant. Traditional breeding methods make use of crossing procedures that rely largely upon observed phenotypic variation to infer causative allele association. That is, traditional plant breeding relies upon observations of expressed phenotype of a given plant to infer underlying genetic cause. These observations are utilized to inform the breeding procedure in order to move allelic variation into germplasm of interest. Further, traditional plant breeding has also been characterized as comprising random mutagenesis techniques, which can be used to introduce genetic variation into a given germplasm. These random mutagenesis techniques may include chemical and/or radiation-based mutagenesis procedures. Consequently, one key feature of traditional plant breeding, is that the breeder does not utilize a genetic engineering tool that directly alters/changes/edits the plant's underlying genetic architecture in a targeted manner, in order to introduce genetic diversity and bring about a phenotypic trait of interest.

The term "plant" refers to whole plants. The term "plant part" include differentiated and undifferentiated tissues including, but not limited to: plant organs, plant tissues, roots, stems, shoots, rootstocks, scions, stipules, petals, leaves, flowers, ovules, pollens, bracts, petioles, internodes, bark, pubescence, tillers, rhizomes, fronds, blades, stamens, fruits, seeds, tumor tissue and plant cells (e.g., single cells, protoplasts, embryos, and callus tissue). Plant cells include, without limitation, cells from seeds, suspension cultures, embryos, meristematic regions, callus tissue, leaves, roots, shoots, gametophytes, sporophytes, pollen and microspores. The plant tissue may be in a plant or in a plant organ, tissue or cell culture.

As used herein when discussing plants, the term "ovule" refers to the female gametophyte, whereas the term "pollen" means the male gametophyte.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, a propagule is any plant material used for the purpose of plant propagation. In asexual reproduction, a propagule is often a stem cutting. In some plants, a leaf section or a portion of root can be used. In sexual reproduction, a propagule is a seed or spore. In micropropagation, a type of asexual reproduction, any part of the plant may be used, though it is usually a highly meristematic part such as root and stem ends or buds.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. The term "plant organ" refers to plant tissue or a group of tissues that constitute a morphologically and functionally distinct part of a plant. "Progeny" comprises any subsequent generation of a plant.

General methods in molecular and cellular biochemistry can be found in such standard textbooks as the following: Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and, Cell and Tissue Culture: Laboratory Procedures in Biotechnology (Doyle & Griffiths, John Wiley & Sons 1998), the disclosures of which are incorporated herein by reference.

The term "pathogen" is used herein in its broadest sense to refer to an organism or an infectious agent whose infection of cells of viable plant tissue elicits a disease response.

As used herein, the term "resistant", or "resistance", describes a plant, line or cultivar that shows fewer or reduced symptoms to a biotic pest or pathogen than a susceptible (or more susceptible) plant, line or variety to that biotic pest or pathogen. These terms are variously applied to describe plants that show no symptoms as well as plants showing some symptoms but that are still able to produce marketable product with an acceptable yield. Some lines that are referred to as resistant are only so in the sense that they may still produce a crop, even though the plants may appear visually stunted and the yield is reduced compared to uninfected plants. As defined by the International Seed Federation (ISF), a non-governmental, non-profit organization representing the seed industry (see "Definition of the Terms Describing the Reaction of Plants to Pests or Pathogens and to Abiotic Stresses for the Vegetable Seed Industry", May 2005), the recognition of whether a plant is affected by or subject to a pest or pathogen can depend on the analytical method employed. Resistance is defined by the ISF as the ability of plant types to restrict the growth and development of a specified pest or pathogen and/or the damage they cause when compared to susceptible plant varieties under similar environmental conditions and pest or pathogen pressure. Resistant plant types may still exhibit some disease symptoms or damage. Two levels of resistance are defined. The term "high/standard resistance" is used for plant varieties that highly restrict the growth and development of the specified pest or pathogen under normal pest or pathogen pressure when compared to susceptible varieties. "Moderate/intermediate resistance" is applied to plant types that restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure. Methods of evaluating resistance are well known to one skilled in the art. Such evaluation may be performed by visual observation of a plant or a plant part (e.g., leaves, roots, flowers, fruits et. al) in determining the severity of symptoms. For example, when each plant is given a resistance score on a scale of 1 to 5 based on the severity of the reaction or symptoms, with 1 being the resistance score applied to the most resistant plants (e.g., no symptoms, or with the least symptoms), and 5 the score applied to the plants with the most severe symptoms, then a line is rated as being resistant when at least 75% of the plants have a resistance score at a 1, 2, or 3 level, while susceptible lines are those having more than 25% of the plants scoring at a 4 or 5 level. If a more detailed visual evaluation is possible, then one can use a scale from 1 to 10 so as to broaden out the range of scores and thereby hopefully provide a greater scoring spread among the plants being evaluated.

In addition to such visual evaluations, disease evaluations can be performed by determining the pathogen bio-density in a plant or plant part using electron microscopy and/or through molecular biological methods, such as protein hybridization (e.g., ELISA, measuring pathogen protein density) and/or nucleic acid hybridization (e.g., RT-PCR, measuring pathogen RNA density). Depending on the particular pathogen/plant combination, a plant may be determined resistant to the pathogen, for example, if it has a pathogen RNA/DNA and/or protein density that is about 50%, or about 40%, or about 30%, or about 20%, or about 10%, or about 5%, or about 2%, or about 1%, or about 0.1%, or about 0.01%, or about 0.001%, or about 0.0001% of the RNA/DNA and/or protein density in a susceptible plant.

Methods used in breeding plants for disease resistance are similar to those used in breeding for other characters. It is necessary to know as much as possible about the nature of inheritance of the resistant characters in the host plant and the existence of physiological races or strains of the pathogen.

As used herein, the term "full resistance" is referred to as complete failure of the pathogen to develop after infection, and may either be the result of failure of the pathogen to enter the cell (no initial infection) or may be the result of failure of the pathogen to multiply in the cell and infect subsequent cells (no subliminal infection, no spread). The presence of full resistance may be determined by establishing the absence of pathogen protein or pathogen RNA in cells of the plant, as well as the absence of any disease symptoms in said plant, upon exposure of said plant to an infective dosage of pathogen (i.e. after 'infection'). Among breeders, this phenotype is often referred to as "immune". "Immunity" as used herein thus refers to a form of resistance characterized by absence of pathogen replication even when the pathogen is actively transferred into cells by e.g. electroporation.

As used herein, the term "partial resistance" is referred to as reduced multiplication of the pathogen in the cell, as reduced (systemic) movement of the pathogen, and/or as reduced symptom development after infection. The presence of partial resistance may be determined by establishing the systemic presence of low concentration of pathogen protein or pathogen RNA in the plant and the presence of decreased or delayed disease-symptoms in said plant upon exposure of said plant to an infective dosage of pathogen. Protein concentration may be determined by using a quantitative detection method (e.g. an ELISA method or a quantitative reverse transcriptase-polymerase chain reaction (RT-PCR)). Among breeders, this phenotype is often referred to as "intermediate resistant."

As used herein, the term "tolerant" is used herein to indicate a phenotype of a plant wherein disease-symptoms remain absent upon exposure of said plant to an infective dosage of pathogen, whereby the presence of a systemic or local pathogen infection, pathogen multiplication, at least the presence of pathogen genomic sequences in cells of said plant and/or genomic integration thereof can be established. Tolerant plants are therefore resistant for symptom expression but symptomless carriers of the pathogen. Sometimes, pathogen sequences may be present or even multiply in plants without causing disease symptoms. This phenomenon is also known as "latent infection". In latent infections, the pathogen may exist in a truly latent non-infectious occult form, possibly as an integrated genome or an episomal agent (so that pathogen protein cannot be found in the cytoplasm, while PCR protocols may indicate the present of pathogen nucleic acid sequences) or as an infectious and continuously replicating agent. A reactivated pathogen may spread and initiate an epidemic among susceptible contacts. The presence of a "latent infection" is indistinguishable from the presence of a "tolerant" phenotype in a plant.

As used herein, the term "susceptible" is used herein to refer to a plant having no or virtually no resistance to the pathogen resulting in entry of the pathogen into the plant and multiplication and systemic spread of the pathogen, resulting in disease symptoms. The term "susceptible" is therefore equivalent to "non-resistant".

As used herein, the term "offspring" refers to any plant resulting as progeny from a vegetative or sexual reproduction from one or more parent plants or descendants thereof. For instance, an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true breeding is homozygous for a trait), while an F2 may be (and usually is) an offspring resulting from self-pollination of said F1 hybrids.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "locus" (plural: "loci") refers to any site that has been defined genetically. A locus may be a gene, or part of a gene, or a DNA sequence that has some regulatory role, and may be occupied by different sequences.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers near an allele is a procedure, which can be performed quite easily by the average person skilled in molecular-biological techniques which techniques are for instance described in Lefebvre and Chevre, 1995; Lorez and Wenzel, 2007, Srivastava and Narula, 2004, Meksem and Kahl, 2005, Phillips and Vasil, 2001. General information concerning AFLP technology can be found in Vos et al. (1995, AFLP: a new technique for DNA fingerprinting, Nucleic Acids Res. 1995 Nov. 11; 23(21): 4407-4414).

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "homologous" or "homolog" is known in the art and refers to related sequences that share a common ancestor or family member and are determined based on the degree of sequence identity. The terms "homology", "homologous", "substantially similar" and "corresponding substantially" are used interchangeably herein. Homologs usually control, mediate, or influence the same or similar biochemical pathways; yet particular homologs may give rise to differing phenotypes. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure, homologous sequences are compared.

The term "homolog" is sometimes used to apply to the relationship between genes separated by the event of speciation (see "ortholog") or to the relationship between genes separated by the event of genetic duplication (see "paralog").

The term "homeolog" refers to a homeologous gene or chromosome, resulting from polyploidy or chromosomal duplication events. This contrasts with the more common 'homolog', which is defined immediately above.

The term "ortholog" refers to genes in different species that evolved from a common ancestral gene by speciation. Normally, orthologs retain the same function in the course of evolution. Identification of orthologs is critical for reliable prediction of gene function in newly sequenced genomes.

The term "paralog" refers to genes related by duplication within a genome. While orthologs generally retain the same function in the course of evolution, paralogs can evolve new functions, even if these are related to the original one.

"Homologous sequences" or "homologs" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.).

As used herein, the term "hybrid" refers to any individual cell, tissue or plant resulting from a cross between parents that differ in one or more genes.

As used herein, the term "inbred" or "inbred line" refers to a relatively true-breeding strain.

The term "single allele converted plant" as used herein refers to those plants that are developed by a plant breeding technique called backcrossing wherein essentially all of the desired morphological and physiological characteristics of an inbred are recovered in addition to the single allele transferred into the inbred via the backcrossing technique.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "mass selection" refers to a form of selection in which individual plants are selected and the next generation propagated from the aggregate of their seeds. More details of mass selection are described herein in the specification.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the term "self-crossing", "self-pollinated" or "self-pollination" means the pollen of one flower on one plant is applied (artificially or naturally) to the ovule (stigma) of the same or a different flower on the same plant.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

II. Strawberries

The garden strawberry, or simply strawberry (*Fragaria* x *ananassa*) is a widely grown hybrid species of the genus *Fragaria*, which are cultivated worldwide for their fruit. Cultivars of *Fragaria* x *ananassa* have replaced the woodland strawberry (*Fragaria vesca*) in large-scale commercial production fields. Pincot et al. (Oct. 1, 2020, Social Network Analysis of the Genealogy of Cultivated Strawberry: Retracing the Wild Roots of Heirloom and Modern Cultivars, Genetics Investigation, 31 pages) studied the pedigree records of 8,851 strawberry genotypes, including 2,656 cultivars developed since 1775. They identified 187 wild octoploid and 1,171 F. x *ananassa* founders in the genealogy they traced from the earliest hybrids to modern cultivars. They estimated that new cultivar selection cycle time over the past 200 years decreased from 16-17 years/generation to 6-10 years/generation.

Strawberries suffer from severe inbreeding depression, and most cultivars are highly heterozygous. Most cultivars are somewhat self-fertile, but good bee activity has been shown to improve pollination. In most cases, the flowers appear hermaphroditic in structure, but function as either male or female. Hermaphrodites contain both male and female functions that enable them to flower, self-pollinate, and bear fruit. Strawberry farmers prefer their plants to be hermaphroditic so they don't have to plant more than one kind of strawberry in the same field in order to have any fruit to harvest.

Strawberries plants are rosette-forming, herbaceous perennials. Strawberries occur in three basic flowering habits: short day, long day and day neutral. These classifications refer to the day length sensitivity of the plant and the type of photoperiod, which induces flower formation. Day neutral cultivars produce flowers regardless of the photoperiod. Most commercial strawberries are either short day or day neutral.

The strawberry is not, from a botanical point of view, a berry. Technically, it is an aggregate accessory fruit, meaning that the fleshy part is derived not from the plant's ovaries but from the receptacle, that holds the ovaries. Each apparent "seed" (achene) on the outside of the fruit is actually one of the ovaries of the flower, with a seed inside it.

Strawberry cultivars vary widely in size, color, flavor, shape, and degree of fertility, season of ripening, and susceptibility or resistance to pests.

There are three main ways to propagate strawberry plants. The plants can be divided and transplanted once multiple crowns have been grown (or division of rhizomes), new plants can be grown from strawberry seeds, or the runners that strawberry plants put out can be controlled, guided and caused to root where clone plants can be utilized most efficiently. Attempting to grow strawberries from the seeds of commercial cultivars will likely not produce true-to-type plants. For purposes of commercial production, plants are propagated from runners and, in general, grown using annual plasticulture, as a perennial system of matted rows or mounds, or using compost socks. Greenhouse and indoor vertical farms produce small amounts of strawberries mostly during the off seasons.

In strawberry breeding and farming, emphasis is placed on sugars, acids and volatile compounds, which improve the taste and fragrance of a ripe strawberry. Strawberries produce many important chemical organic compounds, including, for example, flavonoids, anthocyanins, fructose, glucose, malic acid and citric acid. Esters, terpenes and furans are chemical compounds having the strongest relationships to strawberry flavor and fragrance.

Edger et al. (2019, Origin and evolution of the octoploid strawberry genome. *Nat. Genet.* 51, 541-547) published the first chromosome-scale genome assembly for the octoploid strawberry sequence in February of 2019. The team obtained the 813.4 Mb cultivated commercial strawberry sequence from the California cultivar "Camarosa." Modern strawberries have a complex octoploid genetics (i.e., 8 sets of chromosomes) and sequences for an estimated 7,096 genes (Bombarely et al., 2010, BMC Genomics, 11:503).

For commercial strawberry, the state of the art has matured significantly since publication of the reference genome in 2019 with release of a new SNP array, FanaSNP, which incorporates the subgenome structure of the octoploid. Pincot et al. (Oct. 1, 2020) built on these resources to reconstruct pedigrees and highlight the power and accuracy of diploid Mendelian exclusion analysis for pedigree authentication (paternity and maternity analysis), intellectual property protection, and quality control monitoring of germplasm and nursery stock collections in octoploid strawberry using subgenome-specific DNA markers. They teach that application of these approaches is straightforward because of the simplicity and accuracy of paralog- or homeolog-specific genotyping approaches in octoploid strawberry populations. The development and robustness of subgenome-specific genotyping approaches has enabled the application of standard diploid genetic theory and methods in octoploid strawberry, including the exclusion analysis methods applied in their study.

U.S. Pat. No. 6,274,791 provides methods for *agrobacterium*-mediated transformation and regeneration of strawberry plants using explants prepared from leaves. U.S. Pat. No. 6,043,410 isolated promoters from genomic DNA of strawberry plants and showed that the promoters are capable of tissue-specific expression in transgenic strawberry plants produced via regeneration of apical meristem tissues.

Naing et al. (2019, Plant Methods, 15:36, 10 pages) provide in vitro propagation methods for the production of morphologically and genetically stable plants of different strawberry cultivars using meristem cultures.

III. *Fusarium oxysporum* f. sp. *fragariae*

*Fusarium oxysporum* species complex is a diverse group of filamentous, ascomycetous fungi that are soil borne and able to cause disease in many economically important crop species. *Fusarium oxysporum* f. sp. *fragariae* Winks & Williams (aka *Fusarium fragariae*) is the causal agent of *Fusarium* wilt of strawberry (aka yellows disease).

*Fusarium* wilt is a fungal disease that can wipe out an entire strawberry crop. *Fusarium* wilt may just reduce yields, or, if the plants are under stress from heat and drought, kill an entire strawberry bed or strawberry field. The disease was discovered on strawberries in California in 2006 (Koike et al., 2009, Plant Dis. 93(10): 1077). This common strawberry disease shows up more often in hot and dry weather.

Symptoms of the disease typically include slower growth than normal, stunting, wilting of foliage (particularly of older leaves), crown discoloration, drying and death of older leaves, and eventual plant death (Pastrana et al., 2019, Plant Disease, 103:1249-1251). The youngest leaves in the center of the plant often remain green and alive. Symptoms usually first appear well after plants are established. Plants bearing heavy fruit loads or subjected to stress often show the most severe symptoms. When internal tissues of plant crowns are examined, vascular and cortical tissues are dark to orange-brown. Internal tissues of the main roots are typically not discolored.

Henry et al. (2017, Plant Disease, 1010:550-556) found considerable diversity in their study of 59 isolates of *F. oxysporum* f. sp. *fragariae* obtained from diseased strawberry plants in California. They reported indications that horizontal gene transfer may have occurred. According to Gordon et al. (2015, California Strawberry Commission Annual Production Research Report, Pathology, U. of CA, 15-27), the California population of *F. oxysporum* f. sp. *fragariae* is composed of three somatic compatibility groups (SCG 1, SCG 2 and SCG 3).

Pastrana et al. (2019) demonstrated that *F. oxysporum* f. sp. *fragariae* could move through stolons of infected mother plants and colonize first-generation daughter plants. They also showed that the pathogen could move through stolons from first to second-generation daughter plants and that daughter plants of both generations were symptomless. Henry et al. (2019, Phytopathology, 109:770-779) showed the persistence of *F. oxysporum* f. sp. *fragariae* in soil through asymptomatic colonization of rotation crops. Henry et al. (2020, Plant Pathology, 69(7):1218-1226) also showed that the pathogen can colonize organic matter in soil and persist through anaerobic soil disinfestation.

Gordon et al. (2015) evaluated 15 strawberry cultivars in a field that was naturally infested with the *Fusarium* wilt pathogen. Five cultivars appeared highly resistant in this trial, including 'San Andreas' and 'Portola.' Susceptible cultivars included 'Monterey', 'Albion' and 'Chandler'. They found that the ranking of cultivars based on disease severity was very similar regardless of the isolate with which plants were inoculated.

*F. oxysporum* f. sp. *fragariae* is polyphyletic and limited genetic markers are available for its detection (Burkhardt et al., 2019, Plant Disease, 103:1006-1013).

Pincot et al. (2018, Genome-Wide Association Mapping Uncovers Fw1, a Dominant Gene Conferring Resistance to *Fusarium* Wilt in Strawberry, G3: Genes, Genomes, Genetics, 8(5):1817-1828) reported the discovery of Fw1, a dominant gene conferring resistance to *Fusarium* wilt in strawberry. They mapped the Fw1 locus to the tip of chromosome 2 on subgenome C and released information about multiple SNPs on the iStraw35 array linked to resistance. The AX-166521396 SNP marker was in linkage disequilibrium with the Fw1 gene conferring resistance to *Fusarium* wilt. The AX-166521396 SNP sequence explained 85% of the phenotypic variation for resistance to *Fusarium* wilt in both $S_1$ populations studied. Significant QTL's were not identified elsewhere in the genome. The QTL was completely dominant in one population and nearly completely dominant in the other. AX-166521396 accurately predicted *Fusarium* wilt resistance phenotypes in 97.3% of the germplasm accessions tested, wherein one out of 16 accessions with the A/A genotype and three out of 174 accessions with the A/G genotype were susceptible, whereas seven out of 371 accessions with the G/G genotype were resistant. From the reference genome, the flanking sequence for a PCR assay was identified as: TGCAGGCAGGCAACCCAAATTA-CAGAGATGCTCTTRCAAAGTCCATTCTCTTCTTCC ATGGACAGAGGTCA (SEQ ID NO:1). In SEQ ID NO:1, a nucleotide symbol 'R' represents a purine, that is Guanine (G) or Adenine (A).

IV. Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988). For population improvement methods specific for soybean see, e.g., J. R. Wilcox, editor (1987) SOYBEANS: Improvement, Production, and Uses, Second Edition, American Society of Agronomy, Inc., Crop Science Society of America, Inc., and Soil Science Society of America, Inc., publishers, 888 pages.

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids. As discussed above, hybrid is an individual plant resulting from a cross between parents of differing genotypes. Commercial hybrids are now used extensively in many crops, including corn (maize), sorghum, sugar beet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids that result from crossing those lines. For a detailed discussion of the hybrid production process, see, e.g., Wright, *Commercial Hybrid Seed Production* 8:161-176, In Hybridization of Crop Plants.

Bulk Segregation Analysis (BSA). BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA*, 99:9828-9832) and Quarrie et al. (Quarrie et al., Bulk segregant analysis with molecular markers and its use for improving drought resistance in maize, 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to pathogen), and the other from the individuals having reversed phenotype (e.g., susceptible to pathogen), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Gene Pyramiding. The method to combine into a single genotype a series of target genes identified in different parents is usually referred as gene pyramiding. The first part of a gene pyramiding breeding is called a pedigree and is aimed at cumulating one copy of all target genes in a single genotype (called root genotype). The second part is called the fixation steps and is aimed at fixing the target genes into a homozygous state, that is, to derive the ideal genotype (ideotype) from the root genotype. Gene pyramiding can be combined with marker-assisted selection (MAS, see Hospital et al., 1992, 1997a, and 1997b, and Moreau et al, 1998) or marker based recurrent selection (MBRS, see Hospital et al., 2000).

EXAMPLES

The present disclosure is further illustrated by the following examples that should not be construed as limiting.

Example 1. Breeding of 'Yakima' (a.k.a. '109733')

'Yakima' (a.k.a. '109733') is the result of a controlled-cross between a female parent cultivar designated (Aida', a.k.a. '106734',) an unpatented, proprietary strawberry plant variety made by the inventor and a male parent cultivar designated 'Lili' (a.k.a. '101983' or 'Lily', U.S. Plant Patent No. PP25,849) and was first fruited in Watsonville, Calif. growing fields. Following selection and during testing, the plant was originally designated '109733' and subsequently named 'Yakima'.

The new variety was asexually reproduced via runners (stolons) by the inventor at Watsonville, Calif. Asexual propagules from the original source have been tested in Watsonville growing fields and to a limited extent, grower fields in high elevation. The properties of this variety were found to be transmissible by such asexual reproduction. This cultivar is stable and reproduces true to type in successive generations of asexual reproduction.

Example 2. Morphological and Phenotypic Characteristics of 'Yakima'

The following traits and photographs in combination distinguish the strawberry variety 'Yakima' from known strawberry varieties. In addition, the new cultivar was confirmed to be a unique strawberry germplasm when tested against the California Seed & Plant Lab, Inc. (Elverta, Calif.) database using Short Sequence Repeats (SSRs). Plants for the botanical measurements in the present application were grown as annuals. Any color references are made to The Royal Horticultural Society Colour Chart, 1995 Edition, except where general terms of ordinary dictionary significance are used. The botanical measurements listed in Table 1 were made and recorded during the month of June.

'Yakima' is distinguished from its maternal parent 'Aida' by the shape of its fruit. The fruit of 'Yakima' is mostly conical, different from the longer somewhat flat wedge shape of the fruit of its parent 'Aida'. 'Yakima' is similar to the strawberry plant named 'Monterey' (U.S. Plant Patent No. PP19,767), but possesses several distinguishing traits from Monterey. 'Yakima' is distinguished from 'Monterey' by the thicker canopy of 'Yakima' and dark green foliage color of 'Yakima'. 'Yakima' is a short day (aka vernal) cultivar.

The variety is not reproducible from seed because it is a self-pollinated hermaphroditic and heterozygous genotype.

Explanted meristem cells of 'Yakima' have been grown in Murashigi and Skoog media tubes, have become plantlets, and are suitable for depositing as in-vitro plants. In addition, regeneration of cryopreserved apical stolon tips in tubes held in liquid nitrogen are currently being tested.

DNA extraction of 'Yakima' is currently underway and DNA sequencing will be performed in the near future.

TABLE 1

Characteristics of 'Yakima'.

| Characteristic Type | Characteristic | Yakima |
| --- | --- | --- |
| General | Plant Habit | Annual |
|  | Plant Growth Habit | Upright |
|  | Day length | Short-day |
|  | Planting season | Fall |
|  | Height | 35 cm |
|  | Width | 36 cm |
|  | Density of foliage | Medium |
|  | Plant vigor | High |
|  | Freezing Quality | Moderate |
|  | Rain/weather tolerance | Moderate to high |
|  | Harvest Ease | Moderate |
| Leaf | Leaf Shape | Concave |
|  | Terminal leaflet width | 90 mm |
|  | Terminal leaflet length | 100 mm |
|  | Terminal leaflet length/width ratio | 1.11 |
|  | Teeth per terminal leaflet | 17 to 19 |
|  | Shape of terminal leaflet base | Rounded |
|  | Shape of terminal leaflet in cross-section | Concave to straight |
|  | Shape of terminal leaflet margin | Serrate to crenate |
|  | Color of upper side of leaflet | RHS 136A |
|  | Color of lower side of leaflet | RHS 139C |
|  | Leaf blistering | Weak |
|  | Leaf glossiness | Medium |
|  | Leaf variegation | Absent |
|  | Number of leaflets | 3 leaflets per leaf |
|  | Leaf length | 133 mm |
|  | Leaf width | 151 mm |
|  | Terminal Leaflet margin | Revolute |
|  | Terminal Leaflet shape | Orbicular |
|  | Terminal Leaflet shape of apex | Rounded |
| Limbs | Petiole length | 25.5 cm |
|  | Petiole diameter | 3.18 to 4.26 mm |
|  | Petiole pubescence | Medium |
|  | Petiole pose of hairs | Horizontal |
|  | Petiole color | RHS 145A |
|  | Petiolule length | 1.0 to 1.5 cm |
|  | Petiolule diameter | 2.08 to 2.70 mm |
|  | Stipule length | 3.5 cm |
|  | Stipule width | 0.9 to 1.0 cm |
|  | Stipule pubescence | Dense |
|  | Stipule anthocyanin | Absent |
|  | Stipule color (color code) | RHS 145C |
|  | Pedicel color (color code) | RHS 145A |
|  | Attitude of hairs on peduncle and pedicel | Horizontal to slightly upwards |
|  | Peduncle length | 19.5 cm |
|  | Pedicel length | 13.8 cm |

TABLE 1-continued

Characteristics of 'Yakima'.

| Characteristic Type | Characteristic | Yakima |
|---|---|---|
| Inflorescence | Inflorescence position relative to foliage | Above |
| | Flower arrangement of petals | Touching |
| | Flower size | Medium |
| | Flower diameter | 2.28 cm |
| | Petal shape | Orbicular |
| | Petal apex | Rounded |
| | Petal margin | Entire |
| | Petal base shape | Concave |
| | Petal length | 1.17 cm |
| | Petal width | 1.15 cm |
| | Petal length/width ratio | 1.02 |
| | Petal number per flower | 5 to 7 |
| | Number of flowers | 16 to 36 |
| | Upper Petal color | RHS 155D |
| | Lower Petal color | RHS 155D |
| | Floral Calyx Diameter | 4.08 cm |
| | Corolla diameter | 2.28 cm |
| | Calyx diameter relative to corolla | Larger |
| | Inner calyx | Outer calyx and inner calyx are of equal size |
| | Sepal shape | Elliptical |
| | Sepal apex shape | Acute |
| | Sepal margin | Entire |
| | Sepal length | 1.93 cm |
| | Sepal width | 0.61 cm |
| | Sepal number per flower | 12 |
| | Upper Sepal color | RHS 137A |
| | Lower Sepal color | RHS 137C |
| | Receptacle color | RHS 4A |
| | Fertility | not tested |
| | Time of flowering (50% of plants in bloom) | May |
| | Stigma shape | Rounded |
| | Stigma color | RHS 4A |
| | Style length | 5 mm |
| | Style color | RHS 4A |
| | Ovary color | RHS 138D |
| | Stamen number | 25 |
| | Stamen length | 2.3 mm |
| | Anther shape | Dorsifixed |
| | Anther shape | 1.39 mm |
| | Anther color | RHS 6A |
| | Pollen amount | Scarce to moderate |
| | Pollen color | RHS 163B |
| | Filament color | RHS 145C |
| | Filament length | 1.2 to 2.8 mm |
| Fruit | Fruiting truss length | 6 to 17 cm |
| | Fruiting truss diameter | 1.4 mm |
| | Number of fruit per truss | 1 to 5 |
| | Fruit length | 5.3 cm |
| | Fruit width | 4.3 cm |
| | Fruit skin color | RHS 45A |
| | Fruit flesh color excluding core | RHS 44A |
| | Fruit core color | RHS 41B |
| | Fruit length/width ratio | 1.23 |
| | Fruit weight | 33 g |
| | Relative fruit size | Medium to large |
| | Predominant fruit shape | Long conic and long wedge |
| | Shape difference between primary & secondary fruits | No shape difference |
| | Width of band without of achenes | Narrow |
| | Fruit glossiness | Strong |
| | Position of achenes | Below surface |
| | Achene color | RHS 151D |
| | Achenes per fruit | 340 |
| | Achene weight | 0.238 g |
| | Position of calyx | Even |
| | Fruit Calyx Diameter | 5.5 cm |
| | Level of adherence of calyx | Medium |
| | Color of calyx | RHS 137C |
| | Pose of calyx segments | Reflexed |
| | Size of calyx in relation to fruit | Same |

TABLE 1-continued

Characteristics of 'Yakima'.

| Characteristic Type | Characteristic | Yakima |
|---|---|---|
| | Firmness of flesh | Medium to firm |
| | Evenness of flesh color | Nearly even |
| | Fruit hollow length | 2.3 cm |
| | Fruit hollow width | 1.4 cm |
| | Fruit hollow length/width ratio | 1.64 |
| | Hollow center | Absent to medium |
| | Sweetness | 7 to 14 Brix |
| | pH | 3.33 |
| | Texture when tasted | Fine to medium |
| | Time of flowering | April through August |
| | Time of fruit ripening | May |
| | Harvest maturity (50% of plants with ripe fruit) | June |
| | Type of bearing | Short-day |
| | Grams of fruit per plant | June: 721 g |
| | Yield (lb per acre) | June: 31,791 lb/acre |
| | Firmness | Medium to firm |
| | Surface Texture | Smooth |
| | Appearance Score (rating scale 1 to 5; 5 = best) | 4 |
| | Storage longevity | 5 to 10 days |
| | Cull rate: 1-% Usable | <10% |
| Stolon | Stolon number | 1 to 3 |
| | Stolon length from crown to first daughter | 22.4 cm |
| | Pubescence density | Dense |
| | Intensity of anthocyanin coloration | Absent |
| | Stolon color | RHS N144D |
| Disease Resistance | Plant/fruit disease | Resistant to *Fusarium* wilt |
| | Pest resistance/susceptibility | Resistant to *Fusarium oxysporum* f. sp. *Fragariae*; susceptible to colletotrichum Acutatum |
| Other characteristics | Plant hardness zone | USDA hardiness zone 9b |
| | Shipping quality and fruit market use | The fruit of the Yakima strawberry plant is suitable for shipping and merchandising for distant commercial markets. |
| | Short-day designation | Differentiation of new florescence is required for a prior period of vernalization. (short-day genotype) |

Example 3. Field Testing of 'Yakima'

The 'Yakima' cultivar is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

'Yakima' is distinguished from its paternal parent by the percent of marketable fruit. 'Yakima' percent marketable fruit is twenty percentile points greater than its paternal parent 'Lili' (U.S. Plant Patent No. PP25,849). Table 2 provides the field-testing data for fruit yield and fruit characteristics for 'Yakima' and its male parent 'Lili'.

TABLE 2

Strawberry fruit ("f") summary statistic means of yield, percent marketable, flavor, firmness, figure and size during weeks 15 to 37 over years; Watsonville, California. Fruit height and fruit length are synonymous.

| Variety | Mean fruit height/length (fHeight μmm) | Mean fruit width (fWidth μmm) | Mean fruit height/width (fHeight/fWidth ratio) | Mean hardness in Newtons (N) (μ hardness) | Mean grams per clone (μgrams/clone) |
|---|---|---|---|---|---|
| Yakima | 51.0304 | 40.2999 | 1.26626 | 8.79292 | 1622 |
| Lili | 40.2262 | 35.8540 | 1.12194 | 8.78205 | 1304 |

TABLE 2-continued

Strawberry fruit ("f") summary statistic means of yield, percent marketable, flavor, firmness, figure and size during weeks 15 to 37 over years; Watsonville, California. Fruit height and fruit length are synonymous.

| Variety | Mean fruit height/length (fHeight µmm) | Mean fruit width (fWidth µmm) | Mean fruit height/width (fHeight/fWidth ratio) | Mean hardness in Newtons (N) (µ hardness) | Mean grams per clone (µgrams/clone) |
|---|---|---|---|---|---|

| Variety | Mean Kilos/acre (µkilos/acre) | Mean percent of marketable fruit (µ % Usable) | Mean fruit size in Grams (µ frtSizeGrms) | Mean skin-resistance-to-abrasion categorical rating (µ skin-r) | Mean categorical flavor rating (µ flavor) |
|---|---|---|---|---|---|
| Yakima | 32,443 | 0.905 | 31.39 | 2.13004 | 2.84304 |
| Lili | 26,089 | 0.797 | 29.95 | 2.09745 | 3.05084 |

Example 4. Disease Resistance of 'Yakima'

Given that the yield trials are grown in the same location every year, it is likely that *Fusarium* resistance/susceptibility is involved in the selections being made within the breeding populations that are evaluated. 'Yakima' was first observed to have *Fusarium* wilt resistance in its advanced commercial selection stage when a population of 40,000 clones (about 2 acres) was planted in multiple locations for harvest testing. To date, the parent 'Aida' has not been observed to be resistant or susceptible to this pathogen. The other parent, 'Lili', was grown commercially in many locations over several years and was never observed to present symptoms of *Fragaria*-specific *Fusarium oxysporum*. No relevant information is available regarding the grandparents of 'Yakima'.

Susceptibility trials for *Fusarium* wilt were conducted on many strawberry varieties, including 'Yakima' and its two parents, grown as container stock in sterilized media and inoculated with two isolates. The trial did not provide useful information.

Example 5. Breeding with 'Yakima'

'Yakima' has been used as a parent in subsequent breeding crosses and many newly selected progeny resulting from these crosses are currently in standard yield tests conducted over 24 fruiting weeks and are also entered into morphology phenotype trials. None of these progeny has yet attained advanced commercial standing.

Targeted genomics to achieve a desired genetic gain as it relates to improvement of commercial fruit merchandising qualities, farm yield, and resistance/susceptibility to certain pathogens, including fungal pathogens, can be employed to select among the progeny.

While not wishing to be bound by any particular theory, the resistance to *Fusarium* wilt displayed by 'Yakima' may be due to it having the FwI gene. If so, the AX-166521396 SNP can be used as a genetic marker to select resistant progeny (SEQ ID NO. 1).

DEPOSIT INFORMATION

A deposit of asexual propagules of the strawberry cultivar 'Yakima' of this disclosure is maintained by Sweet Darling Sales, Inc., 24 Seascape Village, Aptos, Calif. 95003. In addition, a sample of the asexual propagules of strawberry cultivar 'Yakima' of this disclosure has been deposited with the NCMA Curator—Patent Deposit, National Center for Marine Algae and Microbiota, Bigelow Laboratory for Ocean Sciences, 60 Bigelow Drive, East Boothbay, Me. 04544, USA (NCMA).

To satisfy the enablement requirements of 35 U.S.C. 112, and to certify that the deposit of the cultivar of the present disclosure meets the criteria set forth in 37 CFR 1.801-1.809, Applicant hereby makes the following statements regarding the deposited strawberry cultivar 'Yakima' (deposited as NCMA Accession No. 202107021).

1. During the pendency of this application, access to the disclosure will be afforded to the Commissioner upon request;

2. All restrictions on availability to the public will be irrevocably removed upon granting of the patent under conditions specified in 37 CFR 1.808;

3. The deposit will be maintained in a public repository for a period of 30 years or 5 years after the last request or for the effective life of the patent, whichever is longer;

4. A test of the viability of the biological material at the time of deposit will be conducted by the public depository under 37 CFR 1.807; and 5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the cultivar will be irrevocably removed by affording access to a deposit of the asexual propagules of the same cultivar with the NCMA.

INCORPORATION BY REFERENCE

All references, articles, publications, patents, patent publications, and patent applications cited herein within the above text and/or cited below are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

What is claimed is:

1. A strawberry breeding method comprising crossing a first strawberry plant with a second strawberry plant to produce progeny plants, growing the progeny plants, and selecting among the progeny plants for progeny plants with resistance to *Fusarium oxysporum*, wherein either the first or second strawberry plant is strawberry cultivar 'Yakima' deposited as NCMA Deposit No. 202107021.

2. The strawberry breeding method of claim 1, wherein the *Fusarium oxysporum* is *Fusarium oxysporum* f. sp. *fragariae*.

3. The strawberry breeding method of claim 1, further comprising selecting among the progeny plants based on one or more of selection criteria based on traits of the strawberry cultivar 'Yakima' wherein the one or more selection criteria are selected from the group consisting of mean fruit height in mm, mean fruit width in mm, ratio of mean fruit height in mm to mean fruit width in mm, mean fruit firmness in newtons, mean fruit appearance score, mean individual fruit weight in grams per plant, and mean combined fruit weight in grams per plant.

4. The strawberry breeding method of claim 1, further comprising producing clones of the progeny plants.

5. The strawberry breeding method of claim 4, further comprising testing the clones for resistance to *Fusarium oxysporum*.

6. The strawberry breeding method of claim 1, further comprising crossing a selected progeny plant with another strawberry plant to produce a strawberry hybrid plant and growing the resultant strawberry hybrid plant.

7. A method for producing a hybrid strawberry plant, or plant part thereof comprising crossing two strawberry plants to produce a hybrid strawberry plant and growing the hybrid strawberry plant, wherein at least one of the two strawberry plants is the strawberry cultivar 'Yakima' deposited as NCMA Deposit No. 202107021.

8. The method of claim 7, wherein the method comprises crossing a plant of the strawberry cultivar 'Yakima' with a different plant of the strawberry cultivar 'Yakima' to produce the hybrid strawberry plant.

9. The method of claim 7, further comprising selecting among the hybrid strawberry plants for hybrid strawberry plants with resistance to *Fusarium oxysporum*.

10. The method of claim 9, wherein the *Fusarium oxysporum* is *Fusarium oxysporum* f. sp. *fragariae*.

11. The method of claim 7, further comprising selecting among the hybrid strawberry plants based on one or more of selection criteria based on traits of the strawberry cultivar 'Yakima' wherein the one or more selection criteria are selected from the group consisting of mean fruit height in mm, mean fruit width in mm, ratio of mean fruit height in mm to mean fruit width in mm, mean fruit firmness in newtons, mean fruit appearance score, mean individual fruit weight in grams per plant, and mean combined fruit weight in grams per plant.

* * * * *

SEQUENCE LISTING

<160> NUMBER OF SEQ ID NOS: 1

<210> SEQ ID NO 1
<211> LENGTH: 71
<212> TYPE: DNA
<213> ORGANISM: Fragaria x ananassa

<400> SEQUENCE: 1
tgcaggcagg caacccaaat tacagagatg ctcttrcaaa gtccattctc ttcttccatg     60
gacagaggtc a                                                         71